(12) United States Patent
Howard (10) Patent No.: US 7,606,445 B2
(45) Date of Patent: Oct. 20, 2009

(54) METHODS AND SYSTEMS FOR ULTRASOUND INSPECTION

(75) Inventor: Patrick Joseph Howard, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 758 days.

(21) Appl. No.: 11/290,649

(22) Filed: Nov. 30, 2005

(65) Prior Publication Data

US 2007/0165918 A1 Jul. 19, 2007

(51) Int. Cl.
*G06K 9/56* (2006.01)

(52) U.S. Cl. .................................................. 382/308
(58) Field of Classification Search ................ 358/3.22, 358/3.23, 3.27, 465, 466; 375/E7.252; 382/172, 382/254–275, 308; 702/193
See application file for complete search history.

(56) References Cited

U.S. PATENT DOCUMENTS

| | | | |
|---|---|---|---|
| 4,986,274 A | 1/1991 | Stephens | |
| 5,482,045 A * | 1/1996 | Rust et al. | 600/437 |
| 5,492,126 A | 2/1996 | Hennige et al. | |
| 5,546,187 A | 8/1996 | Pepper et al. | |
| 5,575,288 A * | 11/1996 | Sliwa et al. | 600/445 |
| 5,760,904 A | 6/1998 | Lorraine et al. | |
| 5,806,521 A * | 9/1998 | Morimoto et al. | 600/447 |
| 5,994,690 A | 11/1999 | Kulkarni et al. | |
| 6,128,092 A | 10/2000 | Levesque et al. | |
| 6,424,597 B1 | 7/2002 | Bolomey et al. | |
| 6,574,304 B1 * | 6/2003 | Hsieh et al. | 378/62 |
| 6,721,448 B2 * | 4/2004 | Rao et al. | 382/164 |
| 6,992,771 B2 * | 1/2006 | Bond et al. | 356/445 |
| 2003/0071750 A1 * | 4/2003 | Benitz | 342/25 |

* cited by examiner

*Primary Examiner*—Matthew C Bella
*Assistant Examiner*—Gregory F Cunningham
(74) *Attorney, Agent, or Firm*—William Scott Andes, Esq.; Armstrong Teasdale LLP (57) ABSTRACT

Methods and systems for measuring indications in an image are provided. The method includes acquiring image data that includes a potential indication, processing the data such that features of the indication are enhanced, thresholding the data such that the indication is separated from the remaining data, determining a size of the indication, and displaying a determined size of the indication.

17 Claims, 5 Drawing Sheets

METHODS AND SYSTEMS FOR ULTRASOUND INSPECTION

BACKGROUND OF THE INVENTION

This invention relates generally to non-destructive testing and, more particularly, to ultrasound inspection of composite parts.

Ultrasonic inspection techniques are used in many applications where non-destructive evaluation of a workpiece is required. One application of such ultrasonic inspection is in the inspection of composite fiber reinforced aircraft engine fan blades. Such blades are typically formed from a plurality of layers of composite fibers (graphite, boron or S-glass, for example) laid over each other and adhesively bonded. Any separation of the fiber layers due to an incomplete bond or void in the blade may detrimentally affect blade strength. Ultrasonic inspection techniques can be used to identify and locate such flaws in a composite fiber reinforced blade. Additionally, ultrasound inspection techniques can be used to inspect composite aircraft engine parts, such as, but not limited to, composite ducts.

In the manufacture of composite materials, anomalous conditions may occur that impact the intended use of the composite material. Such conditions include but are not limited to porosity, delaminations, and foreign material. To detect these anomalous conditions, the composite materials are inspected using an ultrasonic nondestructive testing technique. If the ultrasonic test indicates that an anomalous condition exists, the size of the material anomaly needs to be measured accurately to make an engineering assessment of its impact on the intended use of the composite material.

Using at least some known test methods, the ultrasonic operator determines the boundary points of the material anomaly in the ultrasonic image using his/her best estimate based in the visual appearance of the image. Rules of thumb are typically used to facilitate determining the boundary of the indications. For example, a rule of thumb, such as, all points that are 2 times the mean amplitude of the image pixels surrounding the material anomaly in the image is used.

However such methods tend to reduce accuracy due to for example, a relatively large amount of measurement bias, which in some cases such bias can be approximately 50% of an actual size of the material anomaly. Additionally, such methods have relatively poor repeatability and reproducibility due to operator variability in making the measurements.

BRIEF DESCRIPTION OF THE INVENTION

In one embodiment, a method for measuring indications in an image includes acquiring image data that includes a potential indication, processing the data such that features of the indication are enhanced, thresholding the data such that the indication is separated from the remaining data, determining a size of the indication, and displaying a determined size of the indication.

In another embodiment, an ultrasound inspection system includes a pulse echo transducer, and a processor operationally coupled to the transducer, the processor configured to acquire image data that includes a potential indication, process the data such that features of the indication are enhanced, threshold the data such that the indication is separated from the remaining data, determine a size of the indication, and display a determined size of the indication.

In yet another embodiment, an ultrasound inspection device includes a pulse echo transducer, and a processor operationally coupled to the transducer, the processor configured to process 2D ultrasound data of a part, determine a size and number of indications in the part using morphological operators to threshold and segment the image into clusters of pixels that represent the indications, measure the size of the indications using a bounding box algorithm wherein the bounding box includes the smallest box capable of containing the indications therein, convert the size measurement from a pixel space measurement to a physical dimension, and display the indications and the indication size.

DETAILED DESCRIPTION OF THE INVENTION

Figure 1:
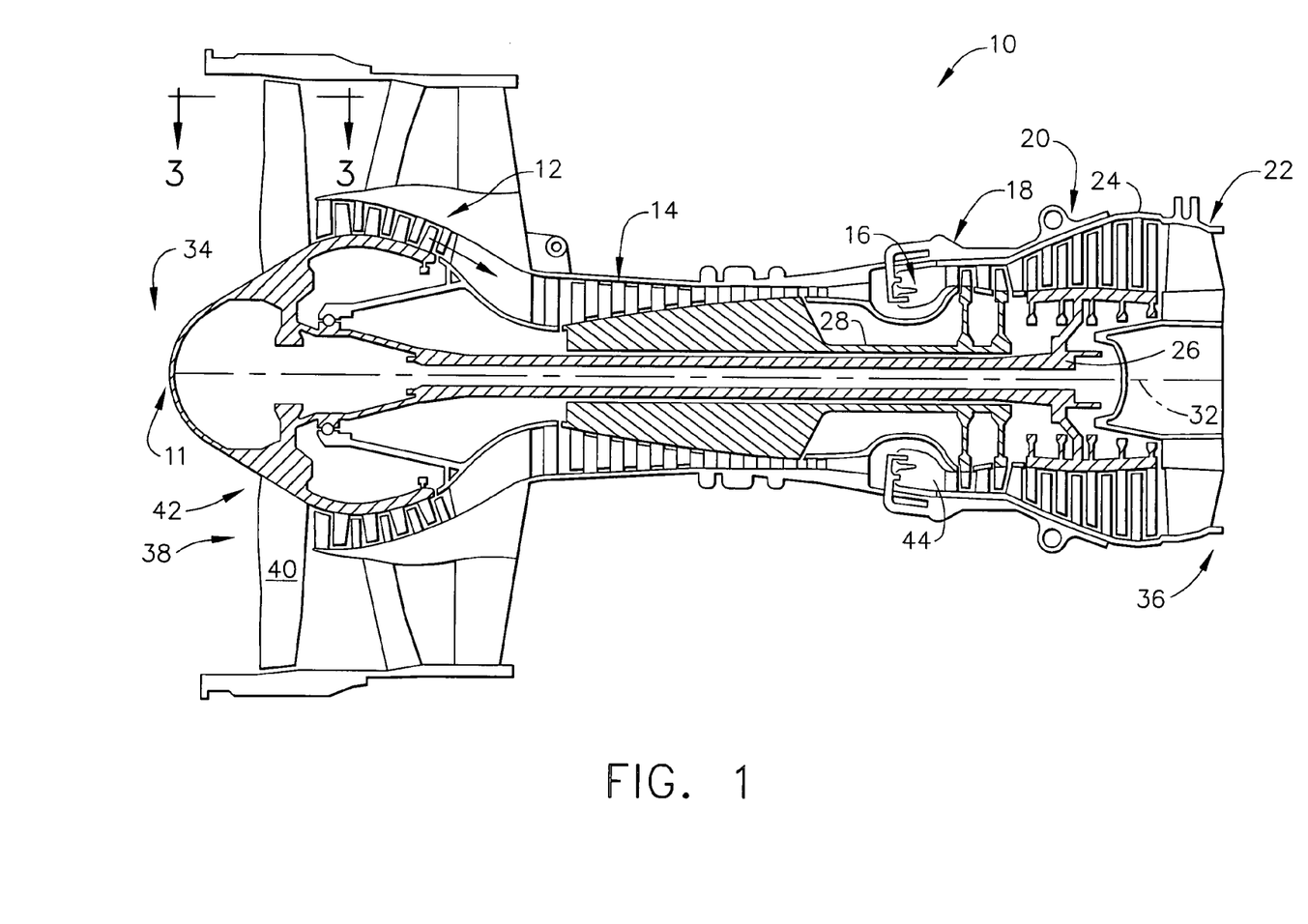
FIG. 1 is a schematic illustration of an exemplary gas turbine engine.

FIG. 1 is a schematic illustration of an exemplary gas turbine engine 10 including a rotor 11 that includes a low-pressure compressor 12, a high-pressure compressor 14 and a combustor 16. Engine 10 also includes a high-pressure turbine 18, a low-pressure turbine 20, an exhaust frame 22 and a casing 24. A first shaft 26 couples low-pressure compressor 12 and low-pressure turbine 20, and a second shaft 28 couples high-pressure compressor 14 and high-pressure turbine 18. Engine 10 has an axis of symmetry 32 extending from an upstream side 34 of engine 10 aft to a downstream side 36 of engine 10. Rotor 11 also includes a fan 38 which includes at least one row of airfoil-shaped fan blades 40 attached to a hub member or disk 42. Blades 40 are substantially identical with respect to each other blade 40 except that there are some small differences due to manufacturing tolerances or defects. Blades 40 are coupled to disk 42 in a substantially equi-angularly spaced relationship to each other. In one embodiment, gas turbine engine 10 is a GE90 engine commercially available from General Electric Company, Cincinnati, Ohio.

In operation, air flows through low-pressure compressor 12 and compressed air is supplied to high-pressure compressor 14. Highly compressed air is delivered to combustor 16. Combustion gases 44 from combustor 16 propel turbines 18 and 20. High pressure turbine 18 rotates second shaft 28 and high pressure compressor 14, while low pressure turbine 20 rotates first shaft 26 and low pressure compressor 12 about axis 32. During some engine operations, such as during take-off operations and other operating periods when engine power output is relatively high, fan 38 rotates such that a radially outer portion of blades 40 attains supersonic velocity. As a result, the supersonically rotating portions of blades 40 may produce shockwaves, which can be heard as noise. The noise may be spread over a broad tonal range, from many multiples of blade passing frequency down to the disk rotational frequency.

Figure 2:
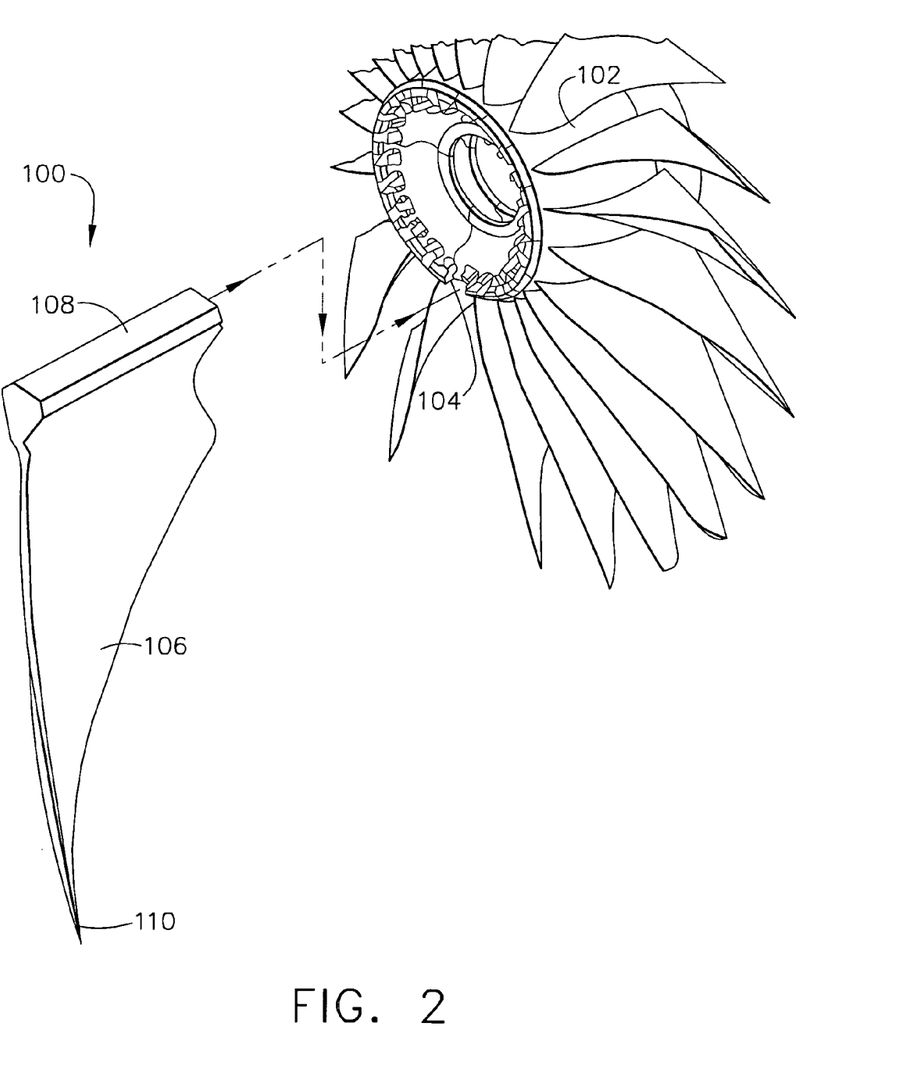
FIG. 2 is an exploded perspective view of an exemplary fan rotor and blading assembly that may be used with the gas turbine engine shown in FIG. 1.

FIG. 2 is an exploded perspective view of an exemplary composite blade 100 and fan rotor disk 102 that may be used with gas turbine engine 10. A plurality of circumferentially-spaced blades 100 are supported by rotor disk or drum 102 through a dovetail slot 104. Each blade 100 includes an airfoil 106 that extends between a dovetail root 108 and a blade tip 110 such that each blade 100 is supported through dovetail root 108 and dovetail slot 104 by rotor 102. Blade 100 is representative of the plurality of circumferentially-spaced blades 100 that are each mapped into a specific slot 104 based on measured parameters of blade 100. In the exemplary embodiment, each blade 100 includes a composite airfoil 106 that includes a plurality of layered composite plies (not shown). More specifically, each blade 100 includes a first plurality of structural and load carrying airfoil plies in airfoil 106 and a second plurality of root plies in root 108.

Figure 3:
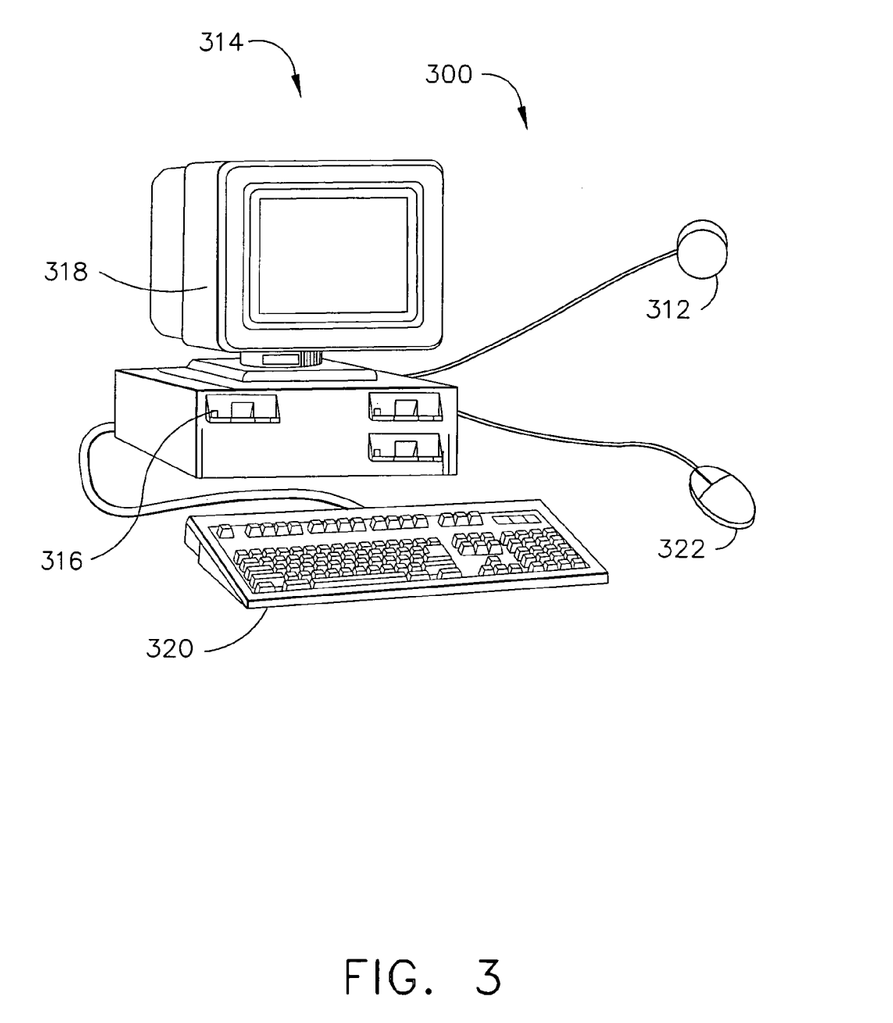
FIG. 3 is a schematic view of an ultrasound system that may be used to analyze and measure anomalies in an object.

FIG. 3 is a schematic view of an ultrasound system 300 that may be used to analyze and measure anomalies in an object. In the exemplary embodiment, system 300 includes a pulse echo transducer 312 coupled to a control unit 314 including a processor 316, a display 318, a keyboard 320 and a mouse 322. In an alternative embodiment, a two-transducer through transmission transducer system is used. In various other embodiments, the transducers are phased-array transducers, single element transducers, or a combination of phased-array and single-element transducers. As used herein, the term processor is not limited to just those integrated circuits referred to in the art as processors, but broadly refers to computers, processors, microcontrollers, microcomputers, programmable logic controllers, application specific integrated circuits, and other programmable circuits. Control unit 314 is configured to acquire, analyze, and display ultrasonic test data. In the exemplary embodiment, ultrasound system 300 is a Pulse echo (PE) ultrasound test apparatus that uses a single transducer located on one side of the component that functions as both a transmitter and a receiver. Using pulse echo testing only requires access to one side of the test component. In various embodiments ultrasound system 300 may include an electromechanical apparatus for moving transducer 312 across the surface of the test component and the electromechanical scanning apparatus may include one or more position sensors that monitor the position of the moving transducer.

In use, transducer 312 is placed in acoustical conduct with a part (not shown) to be tested and ultrasound is introduced into the part. In one embodiment, a known acoustic gel is placed between the part and transducer 312 to facilitate sound transfer between the part and transducer 312. In another embodiment, the part and transducer 312 are placed proximate each other submerged in a liquid that facilitates ultrasound wave travel through the liquid. In an exemplary embodiment using the liquid in an automated setting, system 300 includes a rotatable table (not shown) including at least one collet or mandrel (not shown). The part is automatically chucked in the collet or onto the mandrel and the table is rotated such that the part is in close proximity to transducer 312. Transducer 312 emits ultrasonic energy which is at least partially reflected when an interface is encountered within the part (such as a crack or delamination). In the exemplary embodiment, a dual gantry system is used to collect the data. In an alternative embodiment, a 12-axis dual gantry scanning system is used for scanning parts with complex geometries.

Figure 4:
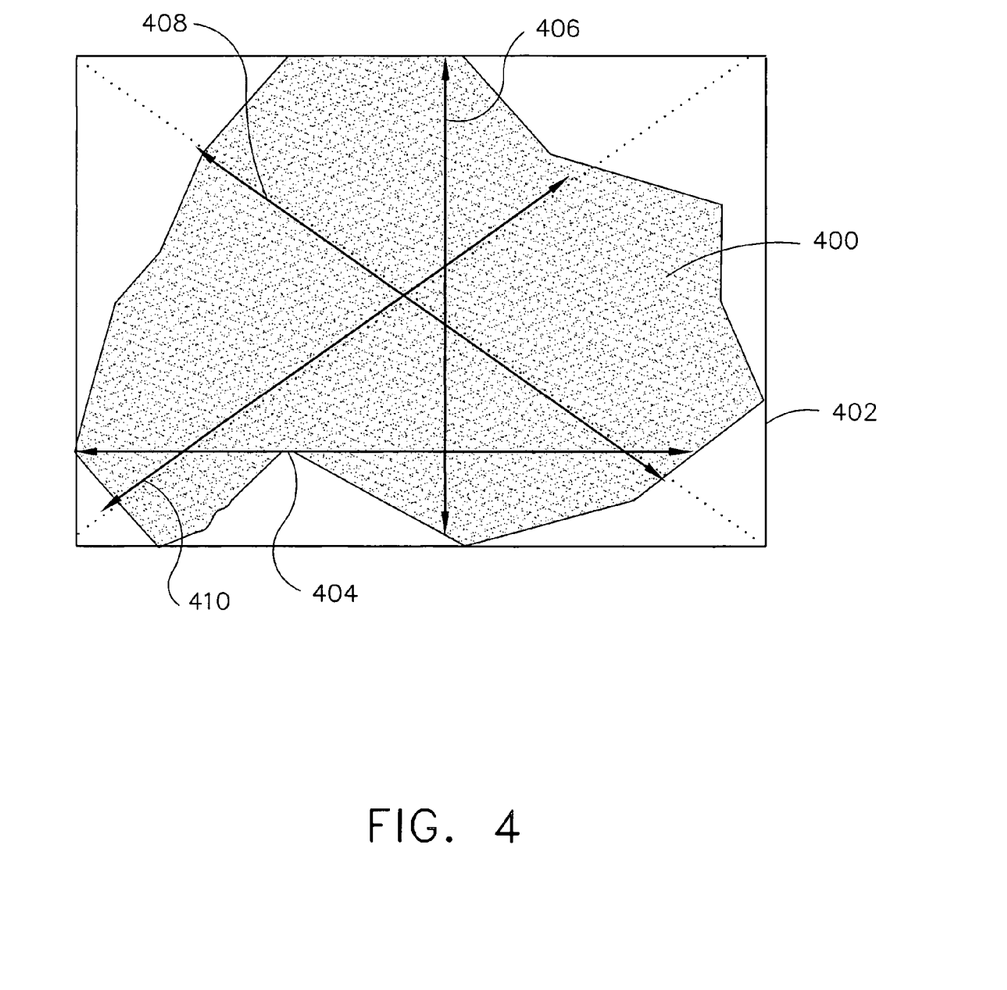
FIG. 4 is a schematic view of an exemplary cluster of pixels that represent one or more indications located within an object under inspection.

FIG. 4 is a schematic view of an exemplary cluster of pixels 400 that represent one or more indications located within an object under inspection. In the exemplary embodiment, the measurements are made using a bounding box 402. Bounding box 402 is the smallest box that completely encloses cluster of pixels 400.

Using the bounding box, a horizontal dimension 404 of the cluster and a vertical dimension 406 of the cluster are determined. These dimensions are calculated as the maximum vertical and horizontal dimension of the cluster within the space of the bounding box. Note that these measurements are not taken using the midpoints of the bounding box in those two directions.

A measurement of the cluster parallel to each of the diagonals, 408 and 410 respectively, of the bounding box are made. The diagonal measurements occur at a single fixed position relative to the bounding box.

The major dimension of the indication is defined as the dimension with the largest measured value. The minor dimension of the indication is the dimension perpendicular to the major dimension. Accordingly, the minor dimension may not be the smallest dimension.

The major and minor dimensions are converted from pixel to physical dimensions such as inches or millimeters. The measurement is divided by the upsample size to be converted back to raw image pixels. The raw image pixel measurement is converted to a physical measurement by multiplying the scan index by the raw measurement in pixels.

Figure 5:
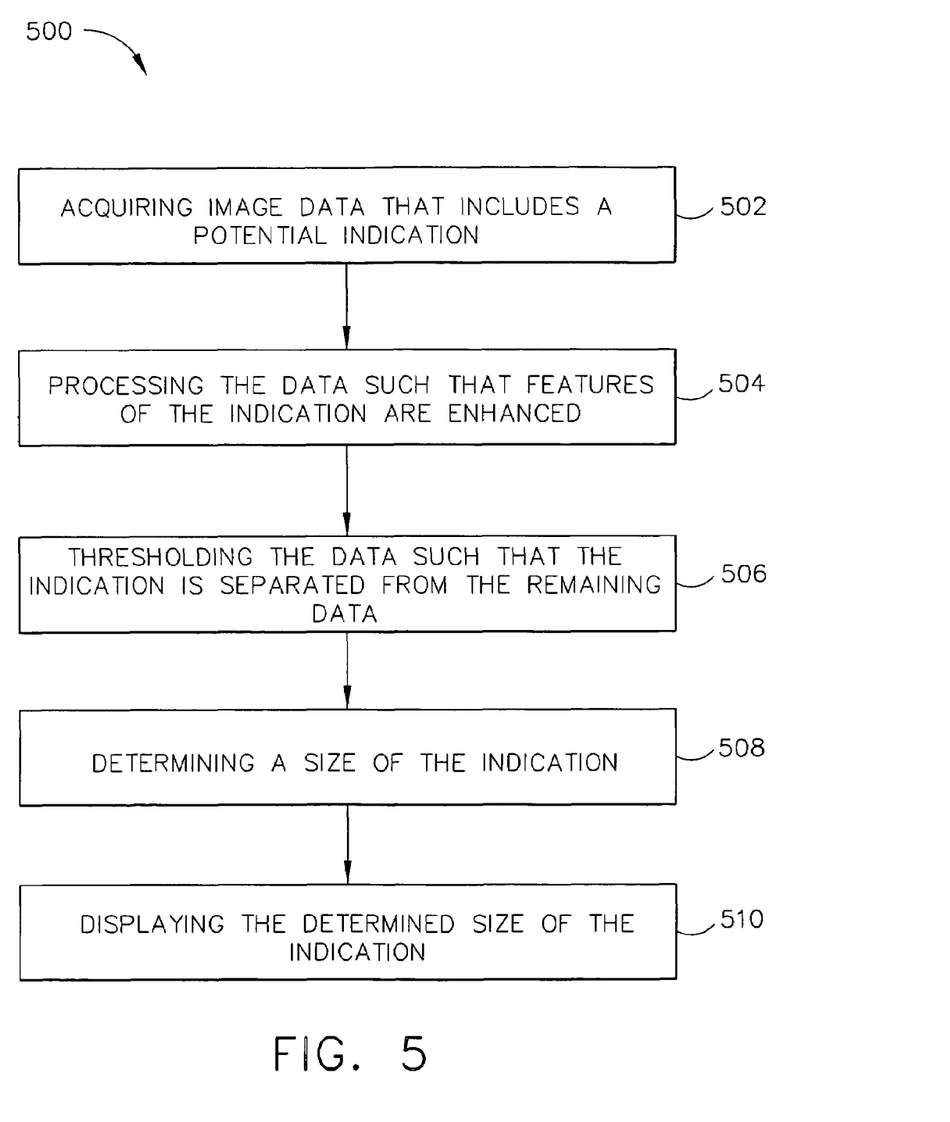
FIG. 5 is a flow diagram of an exemplary method of measuring the size of an indication in an object.

FIG. 5 is a flow diagram of an exemplary method 500 of measuring the size of an indication in an object. The method includes acquiring 502 an ultrasonic inspection data file for the object being inspected. In the exemplary embodiment, this data file is in the form of a 2D image where the two dimensions of the image relate to a spatial position on the object being inspected. The contents of the image represents the ultrasonic response of the transducer at each of the spatial positions in the image. In the exemplary embodiment, the object is a part such as a gas turbine engine fan blade fabricated from a composite material.

An operator analyzes the 2D image data and selects a subset of the image (region of interest (ROI)) that includes data indicative of a material anomaly or indication. There may be more than one ROI in a single set of inspection data. The ROI may also be the entire 2D image in some implementations.

Mathematical algorithms are used to process 504 the image data in the ROI to enhance the features of the material anomaly. The data in the enhanced ROI is thresholded 506 to separate the material anomaly from the rest of the ROI. The algorithm is described in two processes, an Image Preprocessing process and an Image Thresholding and Segmentation process.

In the exemplary embodiment, there are three image pre-processing steps: Noise Reduction, Image Upsampling, and Edge Enhancement. Noise reduction is performed to reduce the impact of electrical noise on the measurement process. In one exemplary embodiment, a standard median filter is used as the lone noise reduction filter. The kernel for the median filter is 3×3.

To increase resolution of the indication measurement step, the noise reduced image is upsampled in each direction. For example, a factor of 4 in each direction may be used with bilinear interpolation.

To enhance the edges of the indication before thresholding, an edge enhancement filter is used. The exemplary inspection uses a Kirsch edge enhancement filter. The size of the Kirsch kernel is 5×5. The coefficients of the north facing Kirsch kernel are given as:

$$k_N = \begin{bmatrix} 11 & 11 & 11 & 11 & 11 \\ -5 & 0 & 0 & 0 & -5 \\ -5 & 0 & 0 & 0 & -5 \\ -5 & 0 & 0 & 0 & -5 \\ -5 & -5 & -5 & -5 & -5 \end{bmatrix}$$

The output of the Kirsch filter is implemented as:

$$K(I) = |I \otimes k_N| + |I \otimes k_S I| + |I \otimes k_E| + |I \otimes k_W|,$$

where $\otimes$ denotes the convolution operator and | | is the absolute value operator. The S, E, W notation represents 90 degree rotations of the kernel $k_N$ defined above.

In the exemplary embodiment, there are three steps in the image thresholding and segmentation process: Amplitude Thresholding, Segmentation, and Relevance Testing. Since the operator is selecting an area of the image with an indication (vs. trying to do automated defect recognition on the whole image), the algorithm includes a variable threshold.

An amplitude threshold is applied to the edge detected image, E. The maximum value of the edge detected image, $E_{max}$, is determined. The threshold level, $T_{level}$, is calculated by multiplying the amplitude threshold, $T_{amp}$, by the maximum value of the edge detected image.

$$T_{level} = E\text{max} * T\text{amp}$$

A binary image, B, is formed by setting all pixels in the binary image to 1 where the corresponding pixel in the edge detected image is greater than the threshold level.

$$B_{(i,j)} = \begin{cases} 1 & \text{for } E_{(i,j)} > T_{level} \\ 0 & \text{for } E_{(i,j)} \le T_{level} \end{cases}$$

After the amplitude thresholding, morphological operators may be applied to the binary image before segmentation occurs. The goals of these operators are to close any small gaps and to fill in any holes.

In the exemplary embodiment, two morphological operators are applied to the image before segmentation occurs. The first is the morphological Close operator. The structuring element for the Close operation is a disk having a predetermined diameter. In the exemplary embodiment, the disk diameter used is based on the gap and the amount of upsampling performed.

The second morphological Fill operation, F( ), is performed on the image. A Fill operation "fills" in any holes in objects in the binary image. Another way to look at it is that any "0" pixels in the binary image that are not connected to the edge of the image are converted to a "1".

Image segmentation is performed on binary image, B after the Fill operation. In this step, all pixels with a value of "1" are segmented into clusters of adjoining pixels. Each cluster is assigned a unique number and the total number of clusters in the image is determined.

Using morphological processing techniques, each cluster in the binary image is compared to the minimum interpretable size for the inspection. If it is equal to or smaller than that size it is eliminated from the binary image.

In the exemplary embodiment, this step is performed using morphological Open operator. The structuring element for this operation is a disk with diameter equal to the minimum interpretable indication in pixels. This diameter is 16 pixels (4 pixel min interpretable×4 pixel upsampling) in this implementation.

In implementations that have anomalies in a wide range of sizes, a variable threshold can be used for this part of the algorithm. The variable threshold is implemented by iterating through the three steps in the image thresholding and segmentation process with progressive lower amplitude thresholds. An initial amplitude threshold specified. This threshold is progressively lowered if no indications above the minimum interpretable size for the inspection are found.

In the exemplary embodiment, the initial value of the amplitude threshold is 50%. The minimum value for the amplitude threshold is 10%. The threshold is reduced in steps of 10% toward this minimum value when no indications are found in the image after the thresholding and segmentation process.

After the clusters are identified, a mathematical algorithm determines 508 the size of each cluster. This size can either be an area or a group of linear dimensions that describe the cluster. In either case, the measurements should be made in physical units such as square inches or square centimeters so that they can be compared to the engineering requirements for the composite part.

In the exemplary embodiment, the measurement of the indication occurs in two phases. First the horizontal, vertical, and diagonal measurements of the remaining cluster are calculated. If more than one distinct cluster remains in the binary image, the clusters are grouped together and treated as one cluster for the measurement process. After the measurements are calculated, the major and minor axes of the indication are determined, and the measurements converted from pixel space to physical dimensions. In the exemplary embodiment, an empirical correction factor is added to the measurement before it is displayed 510 for the user. In an alternative embodiment, the empirical correction is only applied if determined to be necessary to improve an accuracy of the automated measurement.

In the exemplary embodiment, the measurements are based on a bounding box approach. The bounding box for the remaining cluster(s) is the smallest box that completely encloses the remaining cluster(s).

Using the bounding box, the horizontal and vertical dimensions of the cluster are determined. These dimensions are calculated as the maximum vertical and horizontal dimension of the cluster within the space of the bounding box. Note that these measurements are not taken using the midpoints of the bounding box in those two directions.

Next the measurements of the cluster parallel to the diagonals of the bounding box are made. The diagonal measurements occur at a single fixed position relative to the bounding box.

The major dimension of the indication is defined as the dimension with the largest measured value. The minor dimension of the indication is the dimension perpendicular to the major dimension. (It is not necessarily the smallest dimension.)

The major and minor dimensions are converted from pixel to physical dimensions such as inches or millimeters. Any upsampling that occurred is taken into account. The measurement is divided by the upsample size such that the measurement is converted back to raw image pixels. The raw image pixel measurement is converted to a physical measurement by multiplying a scan index by the raw measurement in pixels.

Example embodiments of systems and methods that facilitate locating and quantifying flaws or anomalies in composite airfoils are described above in detail. A technical effect of the systems and methods described herein includes quality control for a fabrication process using nondestructive testing to locate and measure anomalies in the fabricated part.

The above-described ultrasound inspection system is a cost-effective and highly reliable method and system that may be used for ultrasound inspection of composite parts. The method segments image information to locate indication in the part and measures the size of the indication in the image and converts the measurement from pixel space measurement values to physical measurement values. Accordingly, the ultrasound inspection system facilitates fabrication of gas turbine engine components, in a cost-effective and reliable manner.

Exemplary embodiments of ultrasound inspection system components are described above in detail. The components are not limited to the specific embodiments described herein, but rather, components of each system may be utilized independently and separately from other components described herein. Each ultrasound inspection system component can also be used in combination with other ultrasound inspection system components.

What is claimed is:

1. A computer-implemented method of measuring indications in an image, said method comprising:
   acquiring image data that includes an indication;
   processing the data such that features of the indication are enhanced;
   determining a minimum interpretable size for the indication;
   segmenting pixels with a value of "1" into a cluster of adjoining pixels;
   comparing each cluster to the minimum interpretable size using morphological processing techniques;
   eliminating a cluster from the image if the cluster is equal to or smaller than the minimum interpretable size;
   determining a size of the indication; and
   displaying a determined size of the indication.

2. A method in accordance with claim 1 wherein acquiring image data comprises:
   acquiring two dimensional image data; and
   selecting a region of interest of the image data.

3. A method in accordance with claim 1 wherein processing the data comprises applying a median filter having a 3×3 kernel to the image data.

4. A method in accordance with claim 1 wherein processing the data comprises upsampling the image data in each dimensional direction.

5. A method in accordance with claim 1 wherein processing the data comprises applying an edge enhancement filter to the data.

6. A method in accordance with claim 1 wherein processing the data comprises applying a 5×5 Kirsch edge enhancement filter to the data wherein the Kirsch edge enhancement filter is implemented as:

$K(I) = |I \otimes k_N| + |I \otimes k_S| + |I \otimes k_E| + |I \otimes k_W|$, wherein the coefficients of the north facing Kirsch kernel are given as:

$$k_N = \begin{bmatrix} 11 & 11 & 11 & 11 & 11 \\ -5 & 0 & 0 & 0 & -5 \\ -5 & 0 & 0 & 0 & -5 \\ -5 & 0 & 0 & 0 & -5 \\ -5 & -5 & -5 & -5 & -5 \end{bmatrix},$$

where $\otimes$ denotes the convolution operator and $||$ is the absolute value operator. The S, E, W notation represents 90 degree rotations of the kernel $k_N$ defined above.

7. A method in accordance with claim 1 wherein thresholding the data comprises applying an amplitude threshold Tamp to the enhanced image.

8. A method in accordance with claim 7 wherein applying an amplitude threshold to the enhanced image comprises:
   determining a maximum value of the enhanced image, $E_{max}$;
   combining the amplitude threshold, $T_{amp}$ and the maximum value of the enhanced image, $E_{max}$ to determine a threshold level, $T_{level}$;
   generating a binary image, B by setting all pixels in the binary image, B to 1 where the corresponding pixel in the enhanced image, $E_{max}$ is greater than the threshold level, $T_{level}$; and
   applying a morphological operator to binary image, B to at least one of close a gap and fill a hole.

9. A method in accordance with claim 8 wherein applying a morphological operator comprises applying at least one of a morphological close operator and a morphological fill operation.

10. A method in accordance with claim 9 wherein applying a morphological fill operation comprises filling in any holes in objects in the binary image such that "0" pixels in the binary image that are not connected to the edge of the image are converted to a "1".

11. A method in accordance with claim 1 wherein thresholding the data comprises:
   segmenting pixels with a value of "1" are into a cluster of adjoining pixels; and
   assigning a unique identifier to each cluster; and
   tallying a total number of clusters in the image.

12. A method in accordance with claim 1 wherein thresholding the data comprises:
   determining a minimum interpretable size for the indication;
   thresholding and segmenting the image using a first amplitude threshold;
   if no clusters above the minimum interpretable size are found, determining a second amplitude threshold for the indication wherein the second amplitude threshold is less than the first amplitude threshold; and
   iteratively thresholding and segmenting the image using progressively smaller amplitude thresholds until at least one of a predetermined number of clusters is found and a predetermined minimum amplitude threshold is reached.

13. A method in accordance with claim 1 wherein determining a size of the indication comprises:
   if the image includes more than one cluster, grouping the clusters together such that the clusters are measured as one cluster;
   determining a horizontal, vertical, and diagonal measurement of the cluster;
   determining a major and a minor axis of the cluster;
   converting the measurements from pixel space to physical dimensions; and
   applying an empirical correction factor to the measurement.

14. An ultrasound inspection system comprising:
   an ultrasound transducer; and
   a processor operationally coupled to said transducer, said processor configured to:
   acquire image data that includes an indication;

process the data such that features of the indication are enhanced;

apply an amplitude threshold to the enhanced image;

threshold the data such that the indication is separated from the remaining data;

determine a size of the indication;

apply a morphological operator to the image to close gaps and fill holes in the image;

segment the image to generate clusters of pixels that correspond to indications;

compare the clusters to a predetermined minimum interpretable size;

remove from the image, clusters that are smaller than the minimum interpretable size; and measure the size of the clusters using a bounding box algorithm; and display at least one of a determined size of the indication and a measured size of the clusters.

15. A system according to claim 14 wherein said processor is further configured to:

filter the image data to reduce noise;

upsample the image to facilitate increasing the image resolution; and enhance the edges indications in the data using an edge enhancement filter.

16. An ultrasound inspection device comprising:

a pulse echo transducer; and a processor operationally coupled to said transducer, said processor configured to:

process 2D ultrasound data of a part;

determine a size and number of indications in the part using morphological operators to threshold and segment the image into clusters of pixels that represent the indications;

if the image includes more than one cluster, group the clusters together such that the clusters are measured as one cluster;

determine a horizontal, vertical, and diagonal measurement of the cluster;

determine a major and a minor axis of the cluster;

measure the size of the indications using a bounding box algorithm wherein the bounding box comprises the smallest box capable of containing the indications therein;

convert the size measurement from a pixel space measurement to a physical dimension;

apply empirical correction factor to the measurement; and display the indications and the indication size.

17. An ultrasound inspection device in accordance with claim 16 wherein said processor is further configured to:

determine a minimum interpretable size for the indication;

threshold and segment the image using a first amplitude threshold;

if no clusters above the minimum interpretable size are found, determine a second amplitude threshold for the indication wherein the second amplitude threshold is less than the first amplitude threshold; and iteratively threshold and segment the image using progressively smaller amplitude thresholds until at least one of a predetermined number of clusters is found and a predetermined minimum amplitude threshold is reached.

* * * * *

UNITED STATES PATENT AND TRADEMARK OFFICE
CERTIFICATE OF CORRECTION

PATENT NO. : 7,606,445 B2  Page 1 of 1
APPLICATION NO. : 11/290649
DATED : October 20, 2009
INVENTOR(S) : Patrick Joseph Howard It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 994 days.

Signed and Sealed this

Twelfth Day of October, 2010

David J. Kappos
*Director of the United States Patent and Trademark Office*